United States Patent [19]

Clapham

[11] Patent Number: 5,009,660
[45] Date of Patent: Apr. 23, 1991

[54] GAS PURGING, EYE FIXATION HAND PIECE

[75] Inventor: Terrance N. Clapham, Saratoga, Calif.

[73] Assignee: VISX, Incorporated, Sunnyvale, Calif.

[21] Appl. No.: 407,566

[22] Filed: Sep. 15, 1989

[51] Int. Cl.$^5$ .............................................. A61F 9/00
[52] U.S. Cl. ..................................... 606/166; 604/294
[58] Field of Search ...................... 606/10, 13, 15, 16, 606/166, 161, 37, 39, 40; 604/20, 22, 23, 294; 433/80, 81, 91; 269/21

[56] References Cited

U.S. PATENT DOCUMENTS

| | | | |
|---|---|---|---|
| 3,747,216 | 7/1973 | Bassi et al. | 433/81 |
| 4,205,682 | 6/1980 | Crock et al. | 606/166 |
| 4,503,853 | 3/1985 | Ota et al. | 606/16 |
| 4,520,815 | 6/1985 | Marinoff | 606/166 |
| 4,558,698 | 12/1985 | O'Dell . | |
| 4,688,570 | 8/1987 | Kramer et al. | 606/166 |
| 4,718,418 | 1/1988 | L'Esperance, Jr. . | |
| 4,744,362 | 5/1988 | Gründler | 606/166 |
| 4,750,491 | 6/1988 | Kaufman et al. | 606/166 |
| 4,796,623 | 1/1989 | Krasner et al. . | |
| 4,844,060 | 7/1989 | Krumeich | 606/166 |
| 4,919,129 | 4/1990 | Weber, Jr. et al. | 606/37 |

OTHER PUBLICATIONS

Storz brochure, p. 266 showing item E9016, Thornton Fixation Ring.

Primary Examiner—C. Fred Rosenbaum
Assistant Examiner—William W. Lewis
Attorney, Agent, or Firm—Stonebraker, Shepard & Stephens

[57] ABSTRACT

A gas purging, eye fixation hand piece (10) includes a vacuum ring (15) evacuated by a suction line (21) through a handle (20) via which a purging gas is delivered to an array of purging nozzles (36-38) aimed into the vacuum ring from around an inner perimeter of the vacuum ring to direct purging gas jets towards the proximal side (16) of vacuum ring (15) attached to an eye that is held steady in a reference position for laser surgery. A preferably disposable and resilieint eye-engaging ring (25) is removably mounted on the vacuum ring to engage the eye around the cornea, and a spring-biased suction release valve (24) is preferably mounted on hand piece handle (20) for finger operation by the surgeon to release hand piece (10) from the eye when surgery is completed. Mounting of gas purging nozzles (36-38) on the hand piece automatically positions them properly for keeping the cornea clear of particles formed by laser ablation of eye tissue, once hand piece (10) is properly fixed to the eye.

25 Claims, 2 Drawing Sheets

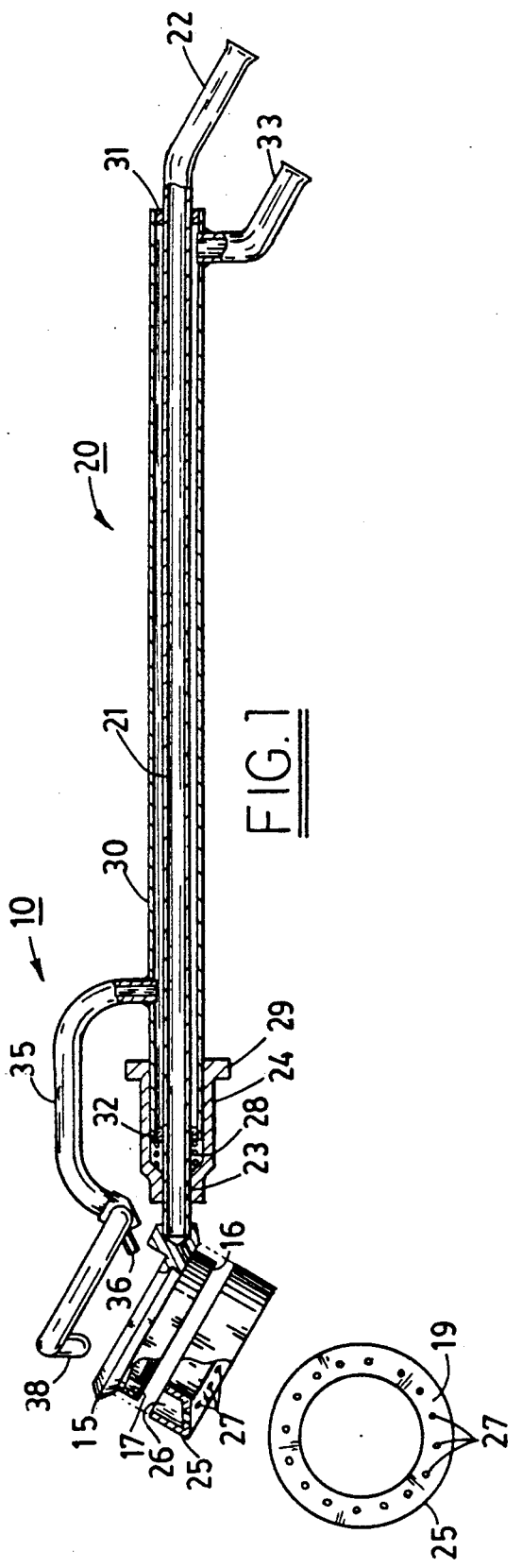
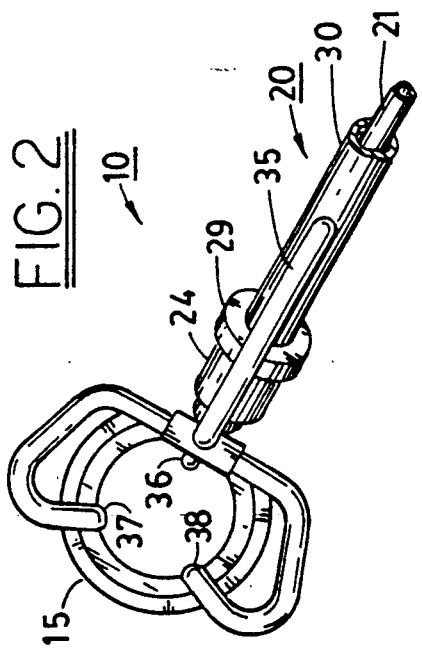
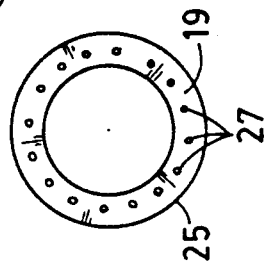

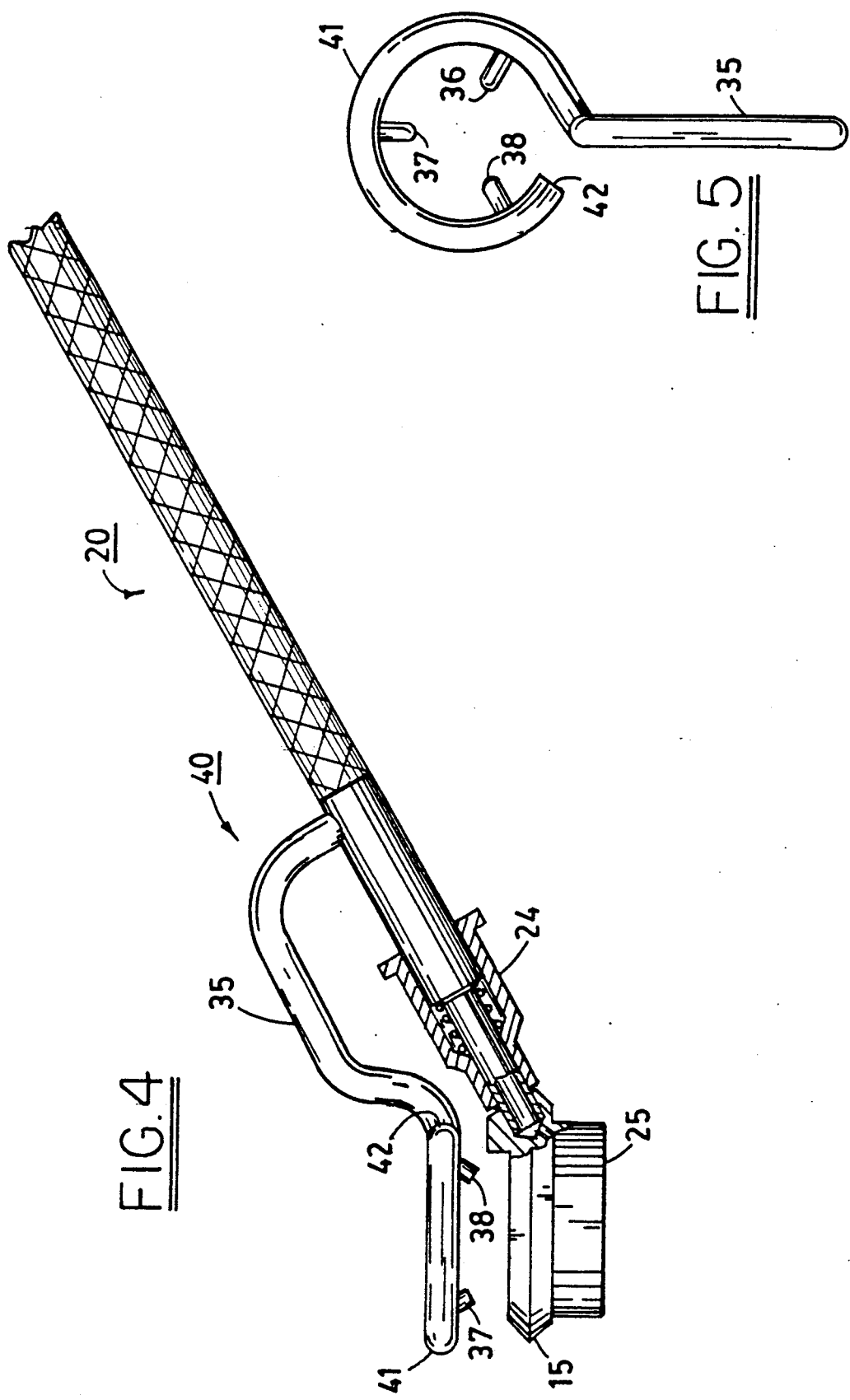

GAS PURGING, EYE FIXATION HAND PIECE

BACKGROUND

Eye fixation hand pieces are used by surgeons for engaging and holding an eye at a fixed reference position during eye surgery. Some of these hand pieces, such as the Thornton fixation ring, engage the eye with barbs. Others, such as the one shown in Krasner U.S. Pat. No. 4,796,623, suggest a vacuum attachment to the eye, but painfully deform the eye between ridges. Vacuum attachment of an eye fixation device is also suggested in FIG. 2 of L'Esperance U.S. Pat. No. 4,718,418 and in O'Dell U.S. Pat. No. 4,558,698; but these are not hand pieces.

We have devised an improved eye fixation hand piece that is especially useful for laser surgery on an eye. Our hand piece makes a secure, but non-painful engagement with the eye, allows the surgeon to hold the eye steady at a fixed reference position during the surgery, and also directs a purging gas jet against the eye to remove tiny particles that are formed as laser pulses ablate away corneal tissue. Our hand piece is also easily disengaged from the eye and accomplishes all its functions conveniently and reliably while allowing the surgeon to view the operating field within a fixation ring.

SUMMARY OF THE INVENTION

Our eye fixation hand piece has a handle extending from a vacuum ring evacuated by a suction line and sized to encircle a cornea of an eye. A proximal side of the vacuum ring engages the eye and is preferably covered by a disposable, resilient eye-engaging ring. The resilient eye-engaging ring is comfortable to the eye and also simplifies the sterilization of the instrument by allowing disposal of the only element that contacts the eye.

By steadying the handle of the eye fixation hand piece, preferably with the aid of a wrist rest, a surgeon can hold an engaged eye in a reference position for surgery. As surgery proceeds with pulses from a laser, corneal tissue within the vacuum ring is ablated into tiny particles that are purged away from the eye by a gas purging nozzle mounted on the hand piece and aimed for directing a purging gas jet into the space within the vacuum ring. Preferably several purging gas jets are arranged around an inner perimeter of the vacuum ring and directed toward the proximal side of the vacuum ring that engages the eye. This directs the purging gas downward into the vacuum ring and against the cornea of the eye to blow the ablation particles upward away from the eye. These are preferably collected in a vacuum device, to keep the surgical area clear of particles.

A line separate from a suction line for the vacuum ring is arranged on the hand piece for delivering purging gas under pressure to one or more purging nozzles. A convenient way of accomplishing this is for the suction line from the vacuum ring to extend through a tubular handle that directs the purging gas to the purging nozzles. For quickly disengaging the vacuum ring from the eye, we prefer a hole arranged in the suction line and covered by a spring-biased valve that can be moved by finger pressure against the bias spring to open the hole to atmosphere. This releases the suction and allows the eyepiece to be removed from the eye.

These features combine to make our eye fixation hand piece especially suitable for eye surgery using a laser.

Our hand piece effectively engages the eye without causing pain, allows the surgeon to hold the eye steady in a reference position without obstructing his view of the cornea, and keeps the cornea clear of particles and gases caused by tissue ablation from the laser pulses. A purging nozzle for this purpose is automatically positioned and aimed properly when the hand piece engages the eye, so that the set-up for surgery is fast and convenient. The hand piece also quickly disengages from the eye when the surgery is finished.

DRAWINGS

FIG. 1 is a partially cut-away and partially exploded view of a preferred embodiment of our gas purging, eye fixation hand piece.

FIG. 2 is a fragmentary perspective view of the eye ring end of the hand piece of FIG. 1.

FIG. 3 is a bottom view of the disposable eye-engaging ring for the hand piece of FIG. 1.

FIG. 4 is a side elevational view of another preferred embodiment of our gas purging, eye fixation hand piece, using a different nozzle assembly.

FIG. 5 is a plan view of the nozzle assembly of the hand piece of FIG. 4.

DETAILED DESCRIPTION

The preferred embodiment 10 of our gas purging, eye fixation hand piece, as shown in FIGS. 1-3, includes a vacuum ring 15 and a handle 20. Vacuum ring 15 is evacuated via a suction line 21 so that ring 15 can be attached to an eye to encircle a cornea. Then, handle 20 can be held steady by a surgeon, preferably using a wrist rest, so that the eye is fixed in a reference position for surgery, which the surgeon can observe via a preferably binocular microscope focused on the cornea of the eye held within ring 15.

Rather than have vacuum ring 15 directly engage the eye, we prefer using a disposable eye-engaging ring 25 that removably fits over the proximal side 16 of vacuum ring 15. Making eye-engaging ring 25 disposable simplifies the sterilization of hand piece 10, since eye-engaging ring 25 is the only element that contacts the eye.

Of the many ways of applying suction to vacuum ring 15 to engage eye ring 25 with an eye, we prefer an evacuated channel 17 formed on the proximal side 16 of vacuum ring 15 so that eye-engaging ring 25 can straddle and fit over the sides of channel 17. We accomplish this with a corresponding and mating channel 26 on eye ring 25 that can slide over and onto the sides of channel 17 in a friction fit and can be removed and disposed of after surgery. A circular array of holes 27 through the eye-engaging surface 19 of eye ring 25 communicates with evacuated channel 17 to secure eye ring 25 to an eye surface by a painless vacuum attachment. This also fixes vacuum ring 15 and the rest of hand piece 10 on the eye, for holding the eye still during surgery.

We prefer that eye-engaging ring 25 be formed of a resilient and flexible material so that it accommodates automatically to slight differences in the shapes of eye surfaces. We have found that molded silicone rubber is a good material for this. It can attach reliably and painlessly to an eye by means of the vacuum applied through holes 27.

The evacuation of channel 17 of vacuum ring 15 is preferably applied by suction line 21 on the free end of which vacuum ring 15 is mounted. Suction line 21 is preferably a pipe extending through handle 20 to an end termination 22 that leads to a vacuum pump. A hole 23 in suction line 21 near vacuum ring 15 is preferably covered by a slide valve 24 that is biased by spring 28 to close hole 23. A flange or grip 29 on valve 24 allows the surgeon to engage and slide valve 24 against the bias of spring 28 to uncover hole 23 and open suction line 21 to atmosphere. This releases the suction on vacuum ring 15 and eye-engaging ring 25 sufficiently to disengage hand piece 10 from the eye when the surgery is completed. This release of hand piece 10 also operates quickly and conveniently, simply by a finger movement of the surgeon.

Handle 20 also includes a tube 30 that preferably surrounds suction line 21, although other arrangements are possible. Both ends 31 and 32 of tube 30 are sealed against suction pipe 21 so that a purging gas delivered under pressure to inlet 33 is contained within tube 30. The pressurized purging gas can be composed of a variety of materials, including dry or moist nitrogen.

The purging gas under pressure within handle tube 30 passes through a delivery pipe 35 to a set of purging nozzles 36-38. A single purging jet nozzle 36 may be adequate, but we prefer three nozzles 36-38 arranged approximately equally spaced around an inner perimeter of vacuum ring 15, as illustrated. Larger and smaller numbers of gas purging nozzles are also possible.

We prefer that nozzles 36-38 be aimed to direct purging gas jets into the space within vacuum ring 15 and to direct the purging gas jets toward the proximal side 16 of vacuum ring 15. In the preferred position for laser surgery of the cornea, the patient is lying prone, with the eye fixed in an upright position so that purging gas jets from nozzles 36-38 are directed downward inside the inner periphery of vacuum ring 15, against the upper surface of the cornea of the eye on which laser pulses are incident Nozzles 36-38 are also preferably arranged clear of the surgeon's field of view into the region within vacuum ring 15, where the surgeon observes, preferably with a microscope.

The purging gas jets from nozzles 36-38 are incident on the cornea of the engaged eye and blow away tiny particles and gases caused by the laser ablation of eye tissue. These are directed upward from the cornea by the combined influence of purging jets from nozzles 36-38; and at a region above vacuum ring 15 and nozzles 36-38, the blownaway particles are preferably vacuumed out of the atmosphere by a vacuum take-up, which is preferably not included in hand piece 10 and is therefore not illustrated in the drawings.

The mounting of nozzles 36-38 on hand piece 10, as illustrated in FIGS. 1-3, automatically positions them properly for surgery, once hand piece 10 is attached to an eye, with ring 25 engaging the eye around the cornea. This saves the surgeon the trouble of setting up and aiming separately mounted gas purging jets, because these are automatically positioned in the proper location once hand piece 10 is properly attached to an eye. Surgery can then proceed quickly while suction in line 21 holds hand piece 10 securely engaged to the eye, and purging gas delivered via pipe 35 is blown against the cornea from nozzles 36-38 to keep the operating field clear. While the surgery proceeds, the surgeon steadies the eye in a reference position by holding handle 20, preferably with the aid of a wrist rest. Corneal surgery with an excimer laser, for example, typically requires only 30 to 60 seconds, after which the surgeon can quickly remove hand piece 10 from the eye by pulling back with a finger on collar 29 of valve 24.

Another preferred embodiment 40 of our gas purging, eye fixation hand piece uses a different nozzle assembly, as shown in FIGS. 4 and 5. Handle 20, vacuum ring 15, and vacuum release valve 24 are the same as described for hand piece 10. The nozzles 36-38 fed by purging gas through delivery pipe 35 are arranged in series around a nearly circular ring 41. Pipe 35 can be formed into ring 41; and each of the nozzles 36-38 are connected to ring 41, to deliver jets of pressurized gas in the same way as previously described. The end 42 of ring 41 is closed so that all purging gas delivered through pipe 35 is jetted through nozzles 36-38.

I claim:

1. In an eye fixation hand piece having a handle extending from a vacuum ring evacuated by a suction line and sized to encircle a cornea of an eye engaged by a proximal side of said vacuum ring so that by steadying the handle, a surgeon can hold the eye in a reference position for surgery, the improvement comprising:
    a. a gas purging nozzle mounted on said hand piece and aimed for directing a purging gas jet into the space within said vacuum ring and toward said proximal side of said vacuum ring; and
    b. a line separate from said suction line arranged on said hand piece for delivering purging gas under pressure to said nozzle to form said purging gas jet.

2. The improvement of claim 1 including a disposable, resilient eye-engaging ring removably mounted on said proximal side of said vacuum ring.

3. The improvement of claim 2 wherein said eye-engaging ring has a circular array of openings communicating with said vacuum ring.

4. The improvement of claim 1 wherein said handle is tubular and said pressurized purging gas is delivered through said tubular handle to said nozzle.

5. The improvement of claim 4 wherein said suction line includes a pipe arranged within said tubular handle.

6. The improvement of claim 1 wherein said handle includes said suction line extending from said vacuum ring and a tubular line for said pressurized purging gas surrounding said suction line for a portion of the length of said handle.

7. The improvement of claim 6 including a spring-biased, finger-operable valve for opening said suction line to atmosphere, for releasing said vacuum ring from said eye.

8. The improvement of claim 7 wherein said suction line has a hole normally covered by said valve and opened to atmosphere by finger movement of said valve against a bias spring.

9. The improvement of claim 1 including a plurality of nozzles for directing a plurality of jets of said purging gas into said vacuum ring from different positions around an inner perimeter of said vacuum ring.

10. A gas purging system for an eye fixation hand piece having an annular vacuum ring sized for encircling a cornea and arranged to be evacuated via a suction line for attaching a proximal side of said vacuum ring to an eye, said gas purging system comprising:
    a. a line for delivering a purging gas to said hand piece;
    b. a nozzle in communication with said purging gas line; and
    c. said nozzle being arranged on said hand piece in the region of an inner perimeter of said vacuum ring to aim a jet of purging gas into the region surrounded by said vacuum ring and toward said proximal side of said vacuum ring.

11. The system of claim 10 including a plurality of nozzles communicating with said purging gas line, each of said nozzles being arranged on said hand piece in the region of said inner perimeter of said vacuum ring so that each nozzle aims a jet of purging gas into said region surrounded by said vacuum ring and toward said proximal side of said vacuum ring.

12. The system of claim 11 wherein said nozzles are approximately evenly spaced around said inner perimeter of said vacuum ring.

13. The system of claim 10 wherein said purging gas line extends through a tubular handle of said hand piece.

14. The system of claim 13 wherein said suction line extends through said tubular hand piece to said vacuum ring.

15. An eye fixation hand piece having a handle extending from a vacuum ring evacuated by a suction line and sized to encircle a cornea of an eye engaged by a proximal side of said vacuum ring so that by steadying the handle, a surgeon can hold the eye in a reference position for surgery, said hand piece comprising:
   a. a disposable, resilient eye-engaging ring removably mounted on said proximal side of said vacuum ring; and
   b. a gas purging nozzle mounted on said hand piece and aimed for directing a purging gas jet into the space within said vacuum ring and toward said proximal side of said vacuum ring.

16. The hand piece of claim 15 including a line separate from said suction line arranged on said hand piece for delivering purging gas under pressure to said nozzle to form said purging gas jet.

17. The hand piece of claim 16 wherein said handle is tubular and said pressurized purging gas is delivered through said tubular handle to said nozzle.

18. The hand piece of claim 17 wherein said suction line includes a pipe arranged within said tubular handle.

19. The hand piece of claim 15 wherein said eye-engaging ring has a circular array of openings communicating with said vacuum ring.

20. The hand piece of claim 19 wherein said eye-engaging ring is molded of silicone rubber.

21. The hand piece of claim 15 wherein said handle includes said suction line extending from said vacuum ring and a tubular line for said pressurized purging gas surrounding said suction line for a portion of the length of said handle.

22. The hand piece of claim 21 including a spring-biased, finger-operable valve for opening said suction line to atmosphere, for releasing said vacuum ring from said eye.

23. The hand piece of claim 21 wherein said suction line has a hole normally covered by said valve and opened to atmosphere by finger movement of said valve against a bias spring.

24. The hand piece of claim 15 including a plurality of nozzles for directing a plurality of jets of said purging gas into said vacuum ring from different positions around an inner perimeter of said vacuum ring.

25. The hand piece of claim 24 wherein said nozzles are approximately evenly spaced around said inner perimeter of said vacuum ring.

* * * * *

UNITED STATES PATENT AND TRADEMARK OFFICE
CERTIFICATE OF CORRECTION

PATENT NO. : 5,009,660

DATED : April 23, 1991

INVENTOR(S) : Terrance N. Clapham and Marguerite B. McDonald

It is certified that error appears in the above-identified patent and that said Letters Patent is hereby corrected as shown below:

```
    Title page, first column, at Inventor, after Calif.,
insert --; Marguerite B. McDonald, New Orleans, La.--.
    Column 4, line 13, delete "I" and insert --We--.
```

Signed and Sealed this

Thirteenth Day of October, 1992

Attest:

DOUGLAS B. COMER

*Attesting Officer*     *Acting Commissioner of Patents and Trademarks*